Figure 1:
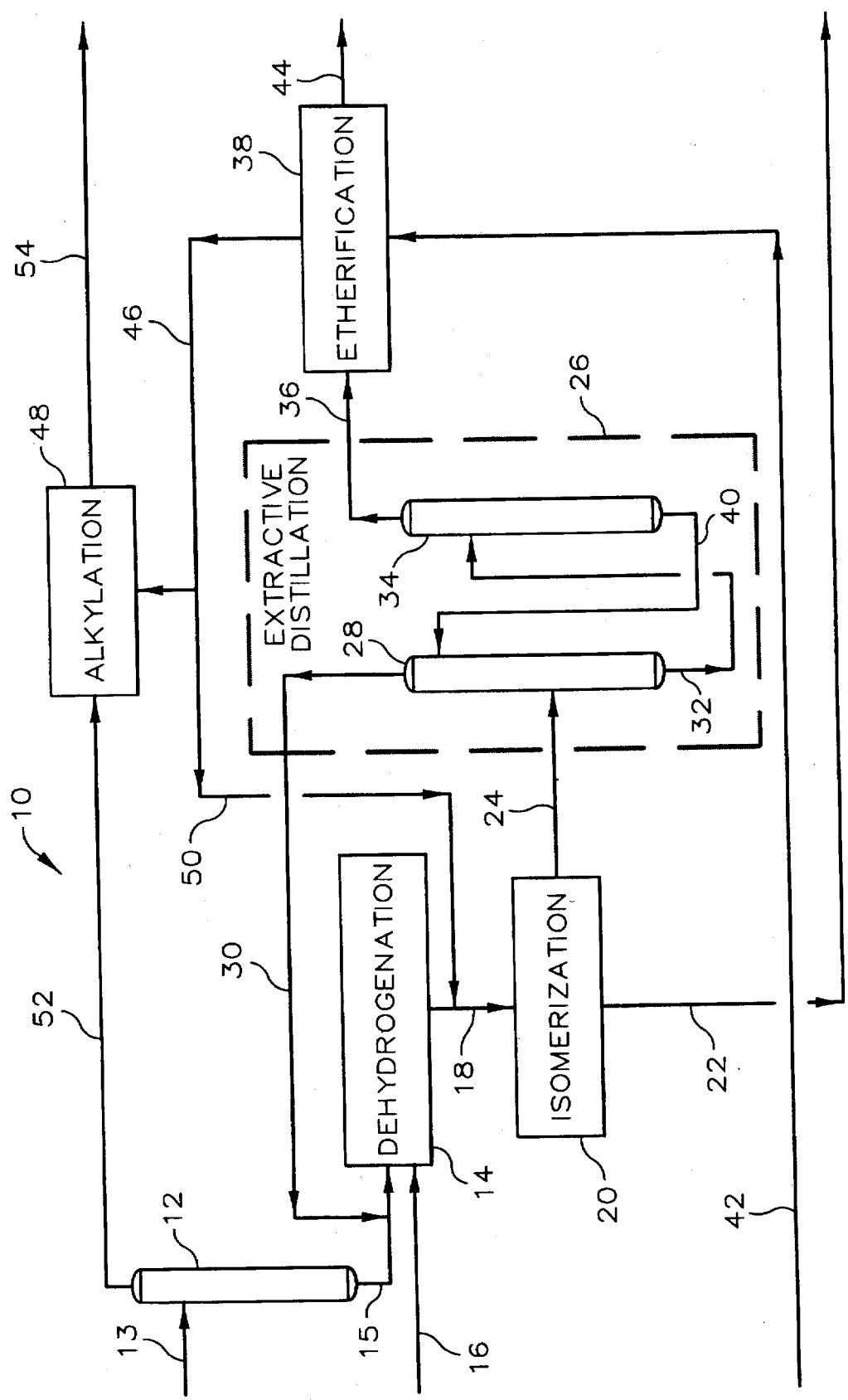

United States Patent [19]
Hunt et al.

[11] Patent Number: 5,689,015
[45] Date of Patent: Nov. 18, 1997

[54] METHOD FOR THE PRODUCTION OF ETHER AND ALKYLATE FROM A PARAFFIN FEEDSTOCK

[75] Inventors: Harold R. Hunt; Mark D. Scharre; Warren M. Ewert, all of Bartlesville, Okla.

[73] Assignee: Phillips Petroleum Company, Bartlesville, Okla.

[21] Appl. No.: 613,267

[22] Filed: Mar. 8, 1996

[51] Int. Cl.[6] .................................................. C07C 41/06
[52] U.S. Cl. .................................. 568/697; 585/315
[58] Field of Search ........................................ 568/697

[56] References Cited

U.S. PATENT DOCUMENTS

| | | | |
|---|---|---|---|
| 4,581,474 | 4/1986 | Hutson, Jr. et al. | 568/697 |
| 4,761,504 | 8/1988 | Pujado | 568/697 |
| 4,797,133 | 1/1989 | Pujado | 44/53 |
| 5,198,097 | 3/1993 | Bogdan et al. | 208/79 |
| 5,254,748 | 10/1993 | Hensley et al. | 568/697 |
| 5,399,787 | 3/1995 | Ozmen et al. | 568/697 |

*Primary Examiner*—Gary Geist
*Assistant Examiner*—S. Padmanabhan
*Attorney, Agent, or Firm*—Charles W. Stewart

[57] ABSTRACT

A process for the production of ethers and alkylate from a paraffin feedstock. The process includes a novel arrangement of dehydrogenation, isomerization, separation, etherification and alkylation to provide such products.

4 Claims, 1 Drawing Sheet

METHOD FOR THE PRODUCTION OF ETHER AND ALKYLATE FROM A PARAFFIN FEEDSTOCK

The present invention relates to a method for manufacturing ether and alkylate from a paraffin feedstock.

Certain ether compounds are known to be desirable gasoline blending components. Among these ether compounds, alkyl tertiary alkyl ether is one of the most desirable for blending with gasoline. Such ether compounds can be prepared by reacting primary or secondary alcohols with olefin compounds having a double bond on a tertiary carbon atom in the presence of an acidic ionic exchange resin catalyst. The particularly more common etherification reactions are those that involve reacting methanol with either isobutylene or isoamylene to form respectively methyl tertiary butyl ether (MTBE) and methyl tertiary amyl ether (TAME). These tertiary alkyl ether compounds are particularly useful as octane improvers for gasoline and, because of their low vapor pressure, they are particularly useful for reducing the vapor pressure of gasoline.

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling said mixture to separate the catalyst from the hydrocarbons, and further separating the hydrocarbons, for example, by fractionation, to recover the alkylation reaction product. Normally, the alkylation reaction product is referred to as "alkylate", and it preferably contains hydrocarbons having seven to nine carbon atoms. In order to have the highest quality gasoline blending stock, it is preferred that the hydrocarbons formed in the alkylation process be highly branched.

It is an object of this invention to provide a process for producing ether compounds and alkylate from a paraffin feedstock.

According to the present invention, an ether product and alkylate product are produced from a mixed butane stream. The mixed butane stream is separated into a n-butane stream and an isobutane stream. The n-butane stream is charged to a dehydrogenation system for dehydrogenating n-butane to provide a product stream containing butenes. The product stream is passed to an isomerization system for isomerizing linear olefins to isoolefins and for producing an isomerate stream containing isoolefins. The isomerate stream is passed to an extractive distillation system in which it undergoes an extractive distillation utilizing a suitable extraction solvent to separate paraffins and olefins and providing a first overhead stream containing n-butane and a second overhead stream containing butenes. The second overhead stream is then passed to an etherification system for reacting isoolefins with a primary alcohol to form ether and to thereby produce a desired ether product containing ether and a raffinate stream containing linear butenes. The raffinate stream and isobutane stream are passed to an alkylation system for reacting isoparaffins and olefin to thereby produce an alkylate stream containing alkylate.

In the accompanying drawing:

FIG. 1 provides a schematic representation of one embodiment of the inventive process.

The inventive process utilizes a novel arrangement of subprocess systems and separation means to give an overall integrated process system that provides for an energy efficient approach to processing butanes so as to produce an ether end-product and an alkylate product. In this process, a mixed butane feed stream is first charged to separation means for separating the mixed butane feed stream into a n-butane stream, comprising n-butane, and an isobutane stream, comprising isobutane. The separation means can be any suitable means which provides for the separation of the mixed butane feed stream into the n-butane stream and isobutene stream, but, preferably, it is a conventional fractionator.

The n-butane stream is charged to a dehydrogenation system for dehydrogenating dehydrogenatable hydrocarbons to produce olefin compounds using a reactor zone containing therein a steam active dehydrogenation catalyst. The n-butane stream is contacted with the steam active dehydrogenation catalyst under process conditions suitable for promoting the dehydrogenation of n-butane to thereby produce a product stream containing butenes.

Any suitable steam active dehydrogenation catalyst can be used, but the most particularly suitable steam active dehydrogenation catalyst comprises (1) a support selected from the group consisting of alumina, silica, magnesia, zirconia, alumina-silicates, Group II aluminate spinels and mixtures thereof and (2) a catalytic amount of at least one Group VIII metal of the Periodic Table of the Elements.

Any catalytically active amount of Group VIII metal can be employed in the steam active dehydrogenation catalysts. Generally the Group VIII metal is present in the catalyst in an amount in the range of about 0.01 to about 10 weight percent of the weight of the support, more often about 0.1 to about 5 weight percent.

Other suitable copromoter metals can also be employed in the steam active dehydrogenation catalyst in conjunction with the Group VIII metal. A preferred type of such co-promoters are Group IVa metal which can be present in the range of about 0.1–1 weight percent of the support, and in one further embodiment, can be present in the range of about 0.1–0.5 weight percent of the support. Although any Group IVa metal, when in compound form, is fully within the scope of this invention, some convenient compounds are the halides, nitrates, oxalates, acetates, carbonates, propionates, tartrates, bromates, chlorates, oxides, hydroxides, and the like of tin, germanium and lead. Tin, itself, is the preferred Group IVa metal and impregnation of the support with tin compounds such as the stannous halides is particularly effective and convenient.

Generally speaking, the Group VIII and Group IVa compounds, which can be combined with the supports to form the catalysts used in the dehydrogenation process can be any compound in which all elements, other than those of Group VIII or Group IVa are volatilized during calcination. These compounds can be sequentially combined with the support, in any order, or for convenience, can be applied simultaneously in a single impregnation operation. After impregnation, the composite solids are dried and calcined.

The dehydrogenation is conducted under any suitable operating conditions. Generally, the dehydrogenation is carried out such that the temperature in the inlet portion of the catalyst beds is at a temperature in the range of from about 900° F. to about 1200° F., preferably from about 950° F. to about 1150° F. The dehydrogenation is also conducted at a pressure in the range of from about 0 to about 200 psig, preferably from about 0 to about 100 psig. Generally, the molar ratio of steam to hydrocarbon is in the range of from about 1/1 to about 25/1, preferably from about 2/1 to 10/1. The use of an externally heated reactor, i.e., a reactor within a fired furnace, enables one to carry out the present invention with the lower levels of steam. The liquid hourly space velocity of hydrocarbon, i.e., volume of hydrocarbon per volume of catalyst per hour, is generally in the range of from about 0.5 to about 10, preferably about 2.0 to about 6.

The product stream from the dehydrogenation trait is charged or passed to an isomerization system for isomerizing at least a portion of the linear butenes, particularly, butene-2, of the product stream to isobutene and to produce an isomerate stream, which contains the isobutene formed by way of the isomerization reaction and other non-reactive paraffins and lesser reactive or even non-reactive butene-1.

The olefin isomerization step includes charging or passing the product stream from the dehydrogenation system, along with water or steam, present in an amount of at least about 0.1 mole of water or steam per mole of olefin, to an isomerization reaction zone of the isomerization system containing an acidic alumina catalyst. The isomerization reaction is an equilibrium type reaction in which butene-2 is isomerized to isobutylene.

The acidic alumina catalysts utilized in the reaction zone of the isomerization system are those known in the art. Preferably, the alumina should have a surface area of at least 50 m$_2$/g. In the practice of the present invention, the alumina is used without the incorporation of substantial amounts of inert solids and does not contain substantial amounts of impurities. Good results are obtained with aluminas having a purity of at least about 99.50 weight percent. The alumina can be in any desired form suitable for contact with the olefin including the example granules, spheres, microspheres, pellets, tablets fluid powder, etc. Preferably alumina catalysts include catalytic beta-alumina and gamma-alumina. The isomerization catalyst can be employed in any manner conventional within the art, such as in a fixed bed, a fluidized bed and the like.

The isomerization reaction can be carried out either batch-wise or continuously, using a fixed catalyst bed, stirred batch reactor, a fluidized catalyst chamber, or other suitable contacting techniques. The isomerization process conditions should be suitable to carry out the conversion of the particular olefin involved. In general, the isomerization reaction can be carried out at a temperature from about 600° F. to about 1200° F., preferably from 850° F. to 1000° F. Any convenient pressure can be used, with the lowest practical pressure preferred in order to minimize side reactions such as polymerization. Pressures ranging from atmospheric to 200 psig are particularly suitable. The LHSV is generally in the range of about 0.1 to 30 volume liquid olefin/volume of catalyst/hr, preferably about 0.2–20.

The isomerate product from the isomerization system, containing isoolefins, particularly isobutene, is passed as a feed to an extractive distillation system. The extractive distillation system is utilized to separate paraffins and olefins, particularly, butanes from butenes. Because the close boiling temperatures of butanes and butenes, extractive distillation is required to be used to perform the separation as opposed to other separation methods such as conventional fractional distillation.

Extractive distillation is a known separation method and is described in detail in literature such as *Perry's Chemical Engineers' Handbook*. Sixth Edition, published by McGraw-Hill Company 1984, page 13–53 through 13–57 and U.S. Pat. No. 3,687,202, both of which are incorporated herein by reference.

Any conventional extraction solvent, which permits the separation of the paraffins and olefins of the isomerate product feed, can be utilized in the extractive distillation system. Examples of suitable extraction solvents include acetonitrile, dimethylformamide, furfural, acetone, dimethylacetamide, n-methylpyrridone, dimethylsulfoxide, sulfolane, and n-formylmorpholine. These solvents can be used alone or with a cosolvent such as water. The preferred extraction solvents include acetonitrile, n-methylpyrridone and sulfolane. The isomerate stream which comprises alkanes and alkenes and, more specifically, comprises linear butenes and butanes, is fed to an extractive distillation tower where it is contacted with a solvent. The solvent alters the relative volatilities of the alkanes and alkenes thereby permitting the separation of such compounds into a first overhead stream, comprising at least one paraffin compound, and a bottoms stream. The bottoms stream from the extractive distillation tower is passed to a stripping tower which provides a second overhead stream comprising at least one olefin. The first overhead stream can be recycled as a feed to the dehydrogenation system for further processing.

The second overhead stream from the extractive distillation system is charged or passed to an etherification system whereby the isoolefins, specifically isobutene, present in the second overhead stream are converted to ethers by reaction with primary or secondary alcohols in the presence of an acid ion exchange resin catalyst.

The alcohols which may be utilized in the etherification reaction include the primary and secondary aliphatic alcohols having from 1 to 12 carbon atoms, such as methanol, ethanol, propanol, isopropanol, the primary and secondary butanols, pentanols, hexanols, ethylene glycol, propylene glycol, butylene glycol, the polyglycols, and glycerol, etc., or mixtures of two or more thereof.

The presently preferred reactants of the etherification reaction are methanol and isobutene because they yield methyl tertiary butyl ether (MTBE) which has utility as an octane improver for gasoline. Another embodiment of this invention includes the use of the reactants ethanol and isobutene to yield ethyl tertiary butyl ether (ETBE).

It is generally preferred for the iso-olefin and the alcohol to be passed through the etherification reaction zone in the presence of diluents which do not have an adverse effect upon the etherification reaction. Examples of suitable diluents include alkanes and straight chain olefins. The feed to the etherification reactor, excluding alcohol, is generally diluted so as to include about 2 to about 80 weight percent iso-olefin, preferably about 10 to about 50 weight percent.

The acid ion-exchange catalysts useful in the etherification reaction zone of the etherification system are relatively high molecular weight carbonaceous material containing at least one SO$_3$H functional group. These catalysts are exemplified by the sulfonated coals "Zeo-Karb H", "Nalcite X" and "Nalcite AX") produced by the treatment of bituminous coals with sulfuric acid and commercially marketed as zeolitic water softeners or base exchangers. These material are usually available in a neutralized form and in this case must be activated to the hydrogen form by treatment with a strong mineral acid such as hydrochloric acid and water washed to remove sodium and chloride ions prior to use. The sulfonated resin type catalyst are preferred for use in the present invention. The catalysts include the reaction products of phenolformaldehyde resins with sulfuric acid ("Amberlite IR-1", "Amberlite IR-100" and "Nalcite MX"). Also useful are the sulfonated resinous polymers of coumarone-indene with cyclopentadiene, sulfonated polymers of coumarone-indene with cyclopentadiene, and furfural and sulfonated polymers of cyclopentadiene and furfural. The most preferred cationic exchange resins are strongly acidic exchange resins consisting essentially of sulfonated polystyrene resin, for instance, divinylbenzene cross-linked polystyrene matrix having from 0.5 to 20 percent and preferably from 4 to 16 percent of copolymerized divinylbenzene therein to which are ionizable or functional nuclear sulfonic acid groups. These reins are manufactured and sold commercially under various trade names such as "Dowex 50", "Nalcite HCR" and "Amberlyst 15". As commercially obtained they have solvent contents of about 50 percent and can be used as is or the solvent can be removed first. The resin particle size is not particularly critical and therefore is chosen in accordance with the manipulative advantages associated with any particular size. Generally mesh sizes of 10 to 50 U.S. Sieve Series are preferred. The reaction may be carried out in either a stirred slurry reactor or in a fixed bed continuous flow reactor. The catalyst concentration in a stirred slurry reactor should be sufficient to provide the desired catalytic effect. Generally catalyst concentration should be 0.5 to 50 percent (dry basis) by weight of the reactor contents with from 1 to 25 percent being the preferred range.

Acid ion exchange resins, such as Rohm & Haas Amberlyst 15 and Dow Chemical Dowex M-31, are currently the most preferred catalysts for the etherification.

The temperature for the etherification reaction zones and the space velocity for the feed to the etherification reactor zone can be selected as desired depending upon the degree of conversion desired and the temperature at which oligomerization becomes a problem. Generally, the temperature of the reaction zone will be in the range of from about 86° F. to about 248° F., preferably from about 95° F. to about 176° F. Pressures are generally selected to ensure that the charges and the products remain in the liquid phase during the reaction. Typical pressures are in the range of from about 30 to about 300 psig. Generally, the liquid hourly space velocity (LHSV) of feed in the reactors will be in the range of about 2 to about 50 hr$^{-1}$.

The molar ratio of alcohol to iso-olefin in etherification system feed will generally be in the range of about 0.5/1 to about 4/1, preferably about 0.8/1 to 1.2/1, most preferably about 1/1.

The etherification reaction zone effluent is passed to a separation system within the etherification system for separating the etherification reaction zone effluent into an ether product stream containing ether and a raffinate stream containing hydrocarbons that did not react within the etherification reaction zone and, preferably, linear butenes. Any suitable separation system known to those skilled in the art can be used to separate the etherification reaction zone effluent to provide the ether product stream and the raffinate stream. Generally, the etherification reaction zone effluent can pass to a conventional fractionator for separating ether from the remaining portion of the etherification reaction zone effluent to give an ether product stream. The remaining portion of the etherification reaction zone effluent is then passed to a solvent extraction system to separate alcohol and hydrocarbons. The alcohol can be recycled as a feed to the etherification reaction zone, and the separated unreacted hydrocarbons passed from the etherification system as the raffinate stream.

The raffinate stream and the isobutane stream are both passed to a alkylation system for reacting isoparaffins and olefins to thereby produce an alkylate stream containing alkylate. The alkylation system is any system which comprises means for alkylating olefins by isoparaffins in the presence of an acid catalyst to produce an alkylate product.

The alkylation reaction generally can be carried out with the hydrocarbon reactants in the liquid phase; however, the reactants need not normally be liquid phase hydrocarbons. The reaction conditions can vary in temperature from sub-zero temperatures to temperatures as high as a few hundred degrees Fahrenheit, and can be carried out at pressures varying from atmospheric to as high as 1,000 p.s.i., and higher. The temperature of the reaction will vary with the reactants and with the catalysts employed, but generally ranges from between about 30° F. to about 150° F., but, preferably from 50° F. to 130° F.

A variety of alkylation catalysts can be employed in the alkylation reaction, including well-known catalysts, such as sulfuric acid, hydrofluoric acid, phosphoric acid; metal halides, such as aluminum chloride, aluminum bromide, etc., and other liquid alkylation catalysts. While generally applicable to the alkylation, the present invention is particularly effective for the alkylation of butenes with saturated branched chain paraffins, such as isobutane, in the presence of hydrofluoric acid.

In the alkylation of isoparaffins and olefins, a substantial molar excess of isoparaffins to olefin is employed, usually to provide a feed ratio in excess of 1:1, usually from about 4:1 to about 20:1 and preferably about 5:1 to 15:1. The reaction zone is maintained under sufficient pressure to ensure that the hydrocarbon reactants and alkylation catalysts are in the liquid phase.

In a further embodiment of the invention, a portion of the raffinate stream can be recycled to the isomerization system whereby the linear olefins are skeletally isomerized to form tertiary olefins which can ultimately serve as a reactive feed in the etherification reactor zones.

Now referring to FIG. 1, there is provided a schematic representation of process system 10 of this invention. A mixed butane feedstream containing normal butane and isobutane is charged to fractionator 12 by way of line 13. Fractionator 12 provides for the separation of the mixed butane feedstream into a n-butane stream, comprising butane, and an isobutane stream, comprising isobutane. The n-butane stream passes from fractionator 12 and is charged to dehydrogenation system 14 by way of line 15. A steam diluent is charged to dehydrogenation system 14 by way of line 16. Passing from dehydrogenation system 14 is the dehydrogenation system 14 product stream by way of line 18.

Within isomerization system 20, the product stream of hydrogenation system 14 undergoes an isomerization reaction and separation whereby the isomerization reactor effluent is processed to form a by-product stream and an isomerate stream. The by-product stream passes from the isomerization system 20 by way of line 22. The isomerate stream passes from isomerization system 20 by way of line 24 to extractive distillation system 26 whereby it undergoes an extractive distillation utilizing a suitable extraction solvent to separate paraffins and olefins.

Extractive distillation system 26 is a conventional extractive distillation system which utilizes a suitable extractive solvent to alter the relative volatilities of the alkanes and alkenes in the isomerate stream in order to assist their separation. Thus, the isomerate stream is charged to extractive distillation column 28 wherein it is contacted with an extraction solvent for removing butenes. The butanes are passed as a first overhead stream by way of line 30 from the extractive distillation column 28. The first overhead stream may be charged as a feed to dehydrogenation system 14. The bottoms product from the extractive distillation column 28 is passed by way of line 32 to stripper column 34. This bottoms stream contains the solvent and butenes removed from the isomerate product stream. Stripper column 34 serves to separate the extraction solvent from the butene. The separated butenes pass as a second overhead stream by way of line 36 to etherification system 38. The bottoms product from stripper column 34 serves as the solvent used in extractive distillation column 28 and is fed to extractive distillation column 28 by way of line 40.

Within etherification system 38, the tertiary butenes will react with an alcohol to form an ether product. Alcohol is therefore fed to the etherification system by way of line 42. The separated ether product passes from the etherification system by way of line 44, and the unreacted linear butenes will pass with the raffinate stream by way of line 46 as a feed to alkylation system 48. A portion of the raffinate stream may optionally be fed to isomerization system 20 by way of line 50. The isobutane stream from fractionator 12 is also passed to alkylation system 48 by way of line 52. An alkylate stream passes from alkylation system 48 by way of line 54.

CALCULATED EXAMPLE

To illustrate the inventive process shown in FIG. 1, this calculated example is provided. The material balance of the calculated example is provided in Table 1. The stream numbers shown in Table 1 correspond to those represented in FIG. 1.

TABLE 1

| Stream | 13 | 15 | 16 | 18 | 22 | 24 | 30 | 36 | 42 | 44 | 46 | 50 | 52 | 54 |
|---|---|---|---|---|---|---|---|---|---|---|---|---|---|---|
| Mass Flow LB/HR | | | | | | | | | | | | | | |
| Lights | 0.00 | 0.00 | 10011.99 | 10349.16 | 10441.16 | 0.00 | 0.00 | 0.00 | 0.00 | 0.00 | 0.00 | 0.00 | 0.00 | 0.00 |
| BD | 0.00 | 0.00 | 0.00 | 79.81 | 0.00 | 0.00 | 0.00 | 0.00 | 0.00 | 0.00 | 0.00 | 0.00 | 0.00 | 0.00 |
| Butene | 0.00 | 0.00 | 0.00 | 3283.19 | 0.00 | 2700.20 | 270.02 | 2430.18 | 0.00 | 0.00 | 2430.18 | 746.95 | 0.00 | 0.00 |
| C4H10 | 1743.70 | 0.00 | 0.00 | 0.00 | 0.00 | 0.00 | 0.00 | 0.00 | 0.00 | 0.00 | 0.00 | 0.00 | 1743.70 | 0.00 |
| C4H10 | 4068.64 | 4068.64 | 0.00 | 4365.64 | 0.00 | 4658.93 | 3727.15 | 931.79 | 0.00 | 0.00 | 931.79 | 286.40 | 0.00 | 645.39 |
| C5+ | 0.00 | 0.00 | 0.00 | 0.00 | 73.15 | 0.00 | 0.00 | 0.00 | 0.00 | 0.00 | 0.00 | 0.00 | 0.00 | 0.00 |
| C16H12 | 0.00 | 0.00 | 0.00 | 0.00 | 75.34 | 0.00 | 0.00 | 0.00 | 0.00 | 0.00 | 0.00 | 0.00 | 0.00 | 0.00 |
| C4H8 | 0.00 | 0.00 | 0.00 | 129.15 | 0.00 | 1291.53 | 129.15 | 1162.38 | 0.00 | 0.00 | 0.00 | 0.00 | 0.00 | 0.00 |
| CH4O | 0.00 | 0.00 | 0.00 | 0.00 | 0.00 | 0.00 | 0.00 | 0.00 | 663.82 | 0.00 | 0.00 | 0.00 | 0.00 | 0.00 |
| MTBE | 0.00 | 0.00 | 0.00 | 0.00 | 0.00 | 0.00 | 0.00 | 0.00 | 0.00 | 1826.19 | 0.00 | 0.00 | 0.00 | 0.00 |
| Alkylate | 0.00 | 0.00 | 0.00 | 0.00 | 0.00 | 0.00 | 0.00 | 0.00 | 0.00 | 0.00 | 0.00 | 0.00 | 0.00 | 3426.93 |
| Total | 5812.34 | 4068.64 | 10011.99 | 18206.95 | 10589.65 | 8650.66 | 4126.32 | 4524.34 | 663.92 | 1826.19 | 3361.97 | 1033.35 | 1743.70 | 4072.31 |

Reasonable variations and modifications are possible within the scope of this disclosure without departing from the scope and spirit thereof.

That which is claimed is:

1. A process comprising the steps of:

(A) separating a mixed butane stream comprising n-butane and isobutane into an isobutane stream, comprising isobutane, and an n-butane stream, comprising n-butane;

(B) charging said n-butane stream to a dehydrogenation system for dehydrogenating n-butane to butene compounds, said dehydrogenation system producing a product stream containing butenes;

(C) passing said product stream to an isomerization system for isomerizing linear butenes to isobutene to thereby produce an isomerate stream containing isobutenes;

(D) passing said isomerate stream to an extractive distillation utilizing a suitable extraction solvent to separate butanes and butenes by providing a first overhead stream, containing butane, and a second overhead stream, containing butenes;

(E) passing said second overhead stream to an etherification system for reacting isobutene with a primary alcohol to form ether and to thereby produce an ether product, containing ether, and a raffinate stream, containing linear butenes; and (F) passing said raffinate stream and said isobutane stream to an alkylation system for reacting isoparaffins and olefins to thereby produce an alkylate stream containing alkylate.

2. A process as recited in claim 1, further comprising the step of:

charging at least a portion of said first overhead stream to said dehydrogenation system.

3. A process as recited in claim 1, further comprising the step of:

passing at least a portion of said raffinate stream to said isomerization system.

4. A process as recited in claim 3, further comprising the step of:

passing at least a portion of said first overhead stream to said dehydrogenation system.

* * * * *